(12) United States Patent
Ma et al.

(10) Patent No.: US 12,265,065 B1
(45) Date of Patent: Apr. 1, 2025

(54) FRACTURE OPENING SIMULATION DEVICE FOR HARD BRITTLE MUDSTONE AND SHALE WITH ORGANIC MATTER

(71) Applicant: Chengdu University of Technology, Chengdu (CN)

(72) Inventors: Yiquan Ma, Chengdu (CN); Yangbo Lu, Chengdu (CN); Ziqi Feng, Chengdu (CN); Yongchao Lu, Chengdu (CN); Lei Chen, Chengdu (CN); Wei Wei, Chengdu (CN); Ying Guo, Chengdu (CN); Chen Zhang, Chengdu (CN); Mingyu Zheng, Chengdu (CN); Lan Yang, Chengdu (CN)

(73) Assignee: Chengdu University of Technology, Chengdu (CN)

( * ) Notice: Subject to any disclaimer, the term of this patent is extended or adjusted under 35 U.S.C. 154(b) by 0 days.

(21) Appl. No.: 18/928,172

(22) Filed: Oct. 28, 2024

(30) Foreign Application Priority Data

Mar. 6, 2024 (CN) .......................... 202410252684.8

(51) Int. Cl.
*G01N 3/10* (2006.01)
*G01N 33/24* (2006.01)

(52) U.S. Cl.
CPC .............. *G01N 3/10* (2013.01); *G01N 33/24* (2013.01); *G01N 2203/0064* (2013.01); *G01N 2203/0067* (2013.01)

(58) Field of Classification Search
CPC .. G01N 3/10; G01N 33/24; G01N 2203/0064; G01N 2203/0067
See application file for complete search history.

(56) References Cited

U.S. PATENT DOCUMENTS

| 6,247,358 B1 * | 6/2001 | dos Santos | E21B 49/02 |
| | | | 73/152.11 |
| 10,060,898 B2 * | 8/2018 | Gupta | E02D 1/025 |

FOREIGN PATENT DOCUMENTS

| CN | 103485762 A | 1/2014 |
| CN | 113029793 A | 6/2021 |
| CN | 116556932 A | 8/2023 |

* cited by examiner

*Primary Examiner* — Nguyen Q. Ha
(74) *Attorney, Agent, or Firm* — George D. Morgan (57) ABSTRACT

The invention provides a fracture opening simulation device for hard brittle mudstone and shale with organic matter, it includes a simulated support, the lower part of the simulated support is connected with a storage bucket bottom block plate through a screw, the middle of the simulated support is provided with a support socket with a circular structure, the upper surface of the storage bucket bottom block plate is provided with a circular convex structure of a block plate boss, the block plate boss is closely inserted in the support socket, the upper surface of the simulated support is fixed connected with a core column storage barrel.

4 Claims, 9 Drawing Sheets

FRACTURE OPENING SIMULATION DEVICE FOR HARD BRITTLE MUDSTONE AND SHALE WITH ORGANIC MATTER

CROSS-REFERENCE TO RELATED APPLICATIONS

The application claims priority to Chinese patent application No. 202410252684.8, filed on Mar. 6, 2024, the entire contents of which are incorporated herein by reference.

TECHNICAL FIELD

The present invention relates to the technical field of hard brittle mudstone and shale research tools, and particularly to a fracture opening simulation device for hard brittle mudstone and shale with organic matter.

BACKGROUND

Hard brittle mudstone and shale are the complex rock, mainly composed of organic matter, clay minerals and rock minerals. In the drilling process, hard brittle mudstone and shale will be affected by the geomechanics environment, hydration, stress, temperature and other factors, resulting in changes in mineral crystal structure, and then change the mineral chemical composition. Through the fracture opening test of hard and brittle mudstone and shale, the law and influencing factors of the fracture opening of hard and brittle mudstone and shale can be obtained, which provides reference for practical engineering application. In the simulation test, the fracture opening of hard and brittle mudstone and shale, the change of structure and the formation of pore network, and the mechanism of hole wall instability can be observed by changing the fluid pressure.

In the crack opening simulation test of the existing hard and brittle mudstone and shale, the core column is sampled and stored in a test vessel, the test fluid is filled inside the experimental vessel, and the fluid is applied with varying hydraulic pressure, and then the crack situation of the core column for the test is observed. However, the traditional test vessel has a fixed structure and does not have the same variable pressure as the extrusion of the rock mass around the mudstone and shale in the natural environment. It is impossible to test the influence of drilling fluid on its shape when drilling in the natural environment, and it is impossible to accurately study the fracture law of hard and brittle mudstone and shale.

SUMMARY

The invention discloses on the first hand, provides a fracture opening simulation device for hard brittle mudstone and shale with organic matter, which includes a simulated support, the lower part of the simulated support is connected with a storage bucket bottom block plate through a screw, the middle of the simulated support is provided with a support socket with a circular structure. The upper surface of the storage bucket bottom block plate is provided with a circular convex structure of the block plate boss, the block plate boss is closely inserted in the support socket, the upper surface of the simulated support is fixed connected with the core column storage barrel, the axis of the core column storage barrel is perpendicular to the upper surface of the simulated support, wherein, The core column storage barrel is connected with two pressure simulation push blocks. The upper end of the core column storage barrel is provided with a storage tube cover plate. The middle of the storage tube cover plate is provided with a drilling fluid pressure chamber, and the axis of the drilling fluid pressure chamber is perpendicular to the upper surface of the storage tube cover plate. The pressure gauge is installed on the upper surface of the storage tube cover plate through screws. The detection end of the pressure gauge is located below the storage tube cover plate. The edge of the storage tube cover plate is connected with two positioning lock plates, and the lower end of the positioning lock plate is connected with the upper edge of the core column storage barrel.

In at least some embodiment, The core column storage barre is a cylindrical structure, the side wall of the core column storage barrel is provided with two guide ports on the side of storage barrel, the side wall of the guide port on the side of storage barrel is parallel to each other, the edge of the outer surface of the core column storage barrel is fixed connected with the upper wedge ring, the cross section of the upper wedge ring is a wedge-shaped structure. The inclined plane of the upper wedge ring is facing outward and above.

In at least some embodiment, The outer cylinder of the core column storage barrel is fixably connected with a limit connecting plate in front and behind, The limit connecting plate is fixed on both sides of a limit guide rod, the limit guide rod is perpendicular to the limit connecting plate, the limit guide rod is connected with the outer end of the guide rod limit end by welding.

In at least some embodiment, The pressure simulation push block on the whole week surrounded by rubber outer layer, The pressure simulation push block sliding connected in the guide port on the side of storage barrel, pressure simulation push block external surface is provided with a simulated push frame, The simulated push frame front and rear respectively fixed connection with a simulated drawing plate, A drawplate guide hole with a circular hole structure is simulated through the simulated drawing plate.

In at least some embodiment, The simulated drawing plate close to the core column storage barrel center side is fixed connected with a push plate tension spring, the push plate tension spring socket on the limit guide rod, the push plate tension spring is fixed connected with the outer end of the positioning lock barrel.

In at least some embodiment, The positioning lock barrel is actively connected with the limit guide rod, the positioning lock barrel is provided with a locking screw hole, the axis of the locking screw hole is perpendicular to the limit guide rod, and the locking screw hole is spirally connected with a locking screw column.

In at least some embodiment, A docking ring groove is arranged on the lower surface of the storage tube cover plate, and the inner part of the docking ring groove is fixed connected with a sealing ring by gluing. The edge of the storage tube cover plate is arranged with two rectangular structure side mouth of the cover plate, and the side mouth of the cover plate is arranged with an articulated socket with a circular hole structure.

In at least some embodiment, The drilling fluid pressure chamber is connected with a pressure input tube, the pressure input tube is installed with a pressure pump, the pressure pump is located above the drilling fluid pressure chamber, the pressure input tube is installed with a flow meter.

In at least some embodiment, the positioning lock plate is L-shaped structure, the positioning lock plate inside the lower edge of the surface processing a locking wedge edge, the locking wedge edge of the wedge face toward the inner and lower, the positioning lock plate is provided with two articulated end blocks, the articulated end block rotation connected in the articulated socket, The positioning lock plate is fixed on the lock plate spring, and the lower end of the lock plate spring is fixed on the upper surface of the storage tube cover plate.

The invention provides a fracture opening simulation device for hard brittle mudstone and shale with organic matter, which has the following beneficial effects:

a) When the fracture opening simulation device for hard brittle shale in the invention is used, the structure of the storage container for the experiment is variable, and the pressure on the inner core column of the container can be exerted through the change of the container structure to simulate the formation confining pressure factor of the core column in the natural environment, so that the simulation test process is closer to the state of the mudstone and shale in the bottom layer in the natural environment. The extrusion force of the core column can be adjusted to simulate the environment of mudstone and shale under different depths and environmental states.

b) The fracture opening simulation device for hard brittle mudstone and shale in the invention is connected with a pressure gauge and a flow gauge, and the pressure of the test fluid added inside the container is detected by the pressure gauge, which is conducive to test recording. The total amount of test fluid entering the drilling fluid pressure chamber is detected by the flow gauge, which is more conducive to test recording and comparison.

c) The fracture opening simulation device for hard brittle mudstone and shale in the invention is composed of multiple parts, which are assembled into the main body of the container by the storage tube cover plate, the core column storage barrel, and the storage bucket bottom block plate. The storage bucket bottom block plate seals the bottom of the core column storage barrel, and the storage tube cover plate is installed at the upper opening of the core column storage barrel. It is convenient to place and seal the core column. When installing the storage tube cover plate, the storage tube cover plate is covered on the top end of the core column storage tube, so that the docking ring groove is docked with the top edge of the core column storage barrel, and the positioning lock plate is inverted inward by the role of the lock plate spring, so that the locking wedge edge automatically fits the core column storage tube, and the storage tube cover plate and the core column storage tube are closely docked by the coordination of the locking wedge edge and the upper wedge ring. When the container is opened at the end of the test, press the plate body of the positioning lock plate above the storage tube cover plate, so that the lower end of the positioning lock plate is turned outward, so that the key structure between the storage tube cover plate and the core column storage barrel is loosens, and the storage tube cover plate is separated from the upper end of the core column storage barrel. The disassembly and assembly of the container are quick, easy to maintain and clean, and it is conducive to improving the efficiency of the test.

BRIEF DESCRIPTION OF DRAWINGS

In order to more clearly explain the technical scheme of the embodiment of the invention, the accompanying drawings of the embodiment will be briefly introduced in the following.

The supplementary drawings described below refer only to some embodiments of the invention and are not limitations of the invention.

In the accompanying picture.

A list of figure markers is attached:
1. simulated support; 101. support socket; 2. core column storage barrel; 201. guide port on the side of storage barrel; 202. upper wedge ring; 203. limit connecting plate; 204. limit guide rod; 205, guide rod limit end; 3, storage bucket bottom block plate; 301. block plate boss; 4, pressure simulation push block; 401, simulated push frame; 402, simulated drawing plate; 403. draw-plate guide hole; 404. push plate tension spring; 405, positioning lock barrel; 406. Locking screw hole; 407, locking screw column; 5, storage tube cover plate; 501. docking ring groove; 502. sealing ring; 503. side mouth of cover plate; 504. articulated socket; 6. drilling fluid pressure chamber; 601, pressure input tube; 602, pressure pump; 603, flow meter; 7, pressure gauge; 8, positioning lock plate; 801, locking wedge edge; 802. articulated end block; 803. lock plate spring.

DETAILED DESCRIPTION OF THE EMBODIMENTS

In order to make the purpose, technical scheme and advantages of the embodiments of the invention more clear, the technical scheme of the embodiments of the invention will be described clearly and completely in the following combined with the attached drawings of the embodiments of the invention. Obviously, the described embodiment is a part embodiment of the invention, but not the whole embodiment. Based on the embodiment of the invention described, all other embodiments obtained by a person of ordinary skill in the art without creative labor shall fall within the scope of the protection of the invention.

Figure 1:
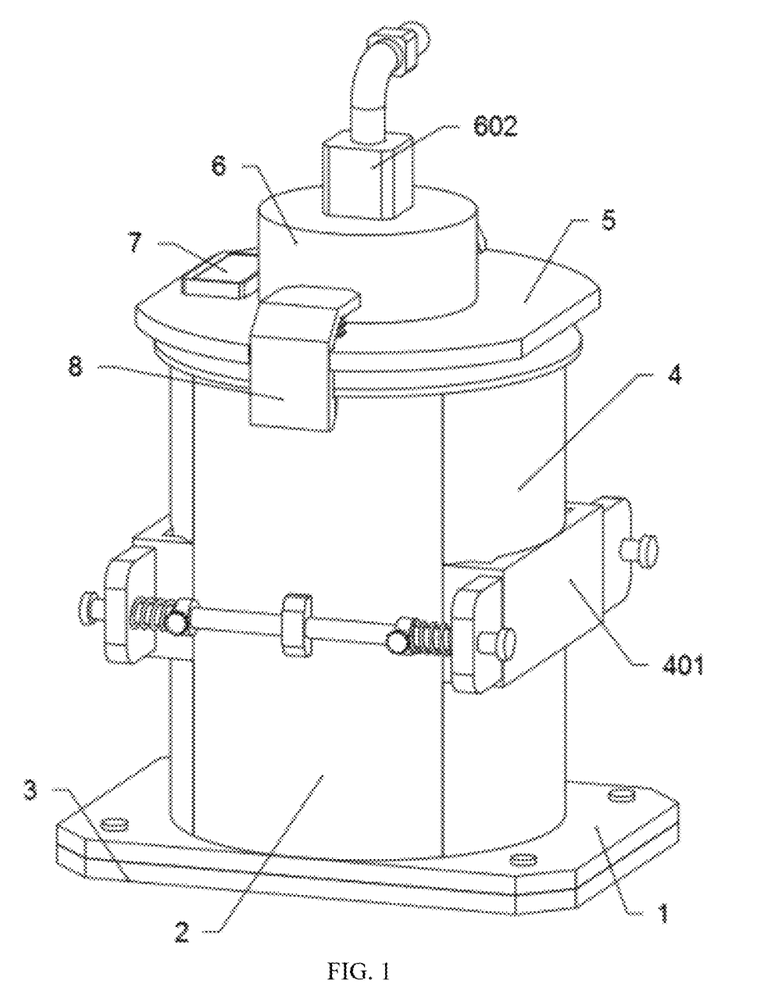
FIG. 1 shows a schematic diagram of the overall structure of the application.
Figure 2:
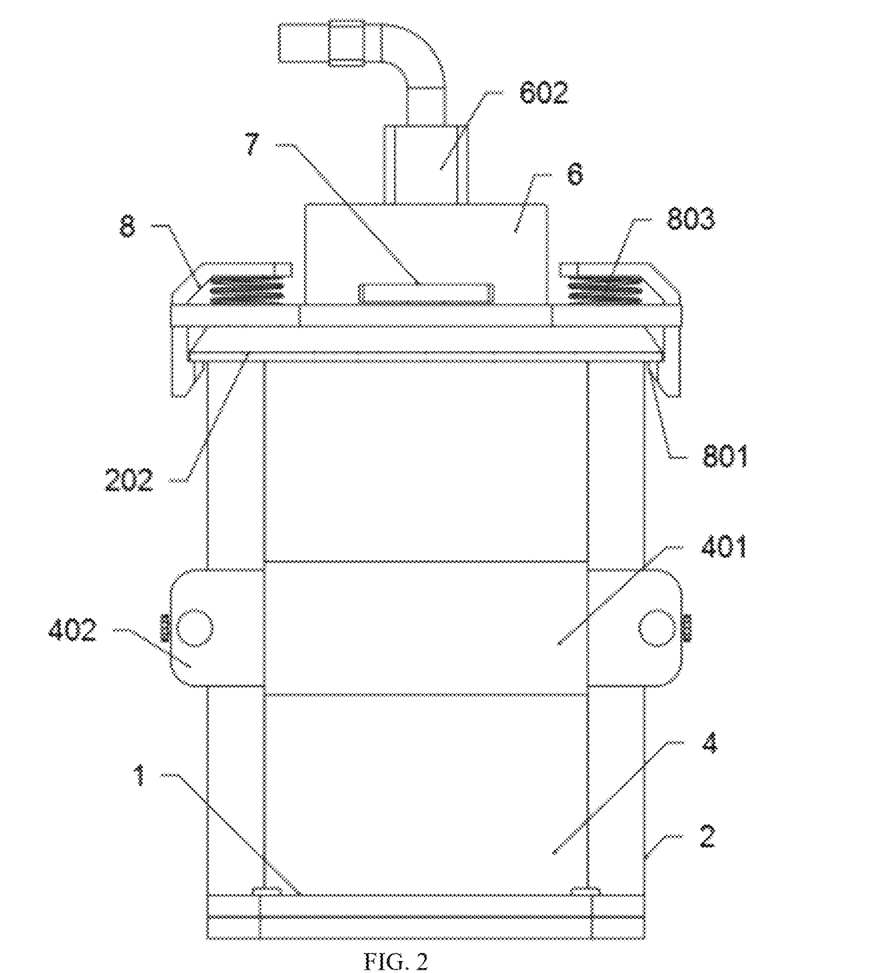
FIG. 2 shows the structure diagram of the left view of FIG. 1 of this application.
Figure 3:
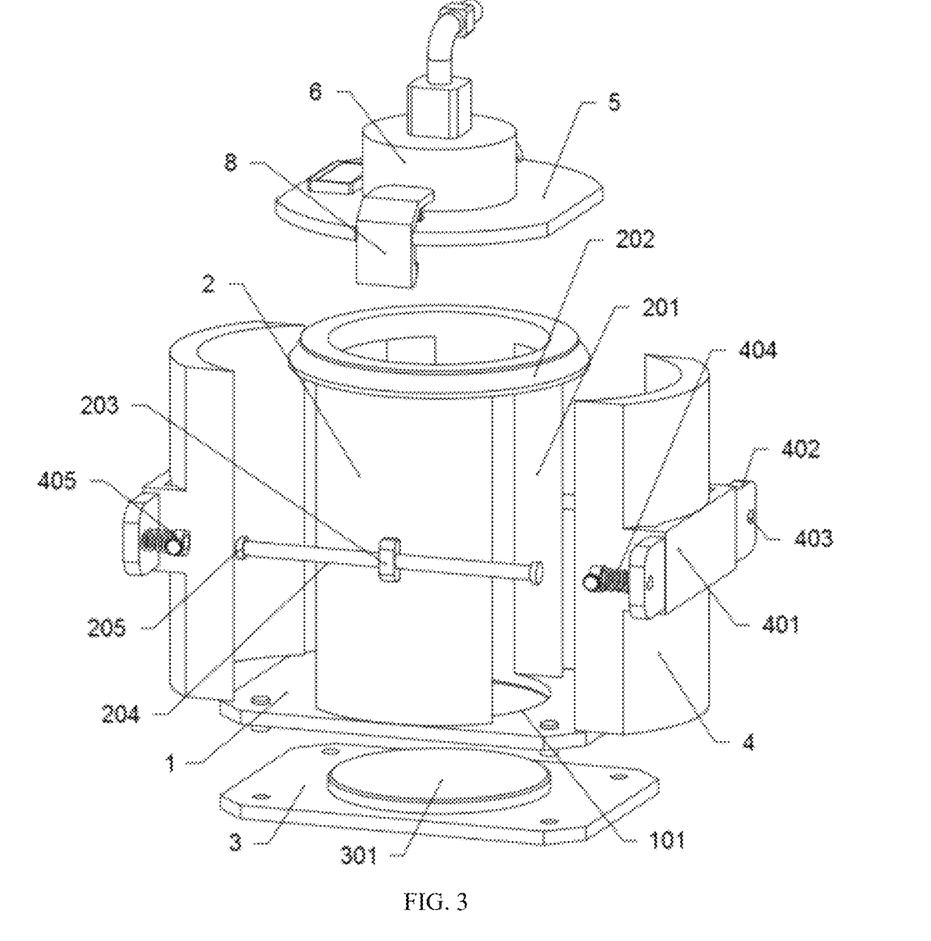
FIG. 3 shows the structure diagram of this application in the decomposed state.
Figure 4:
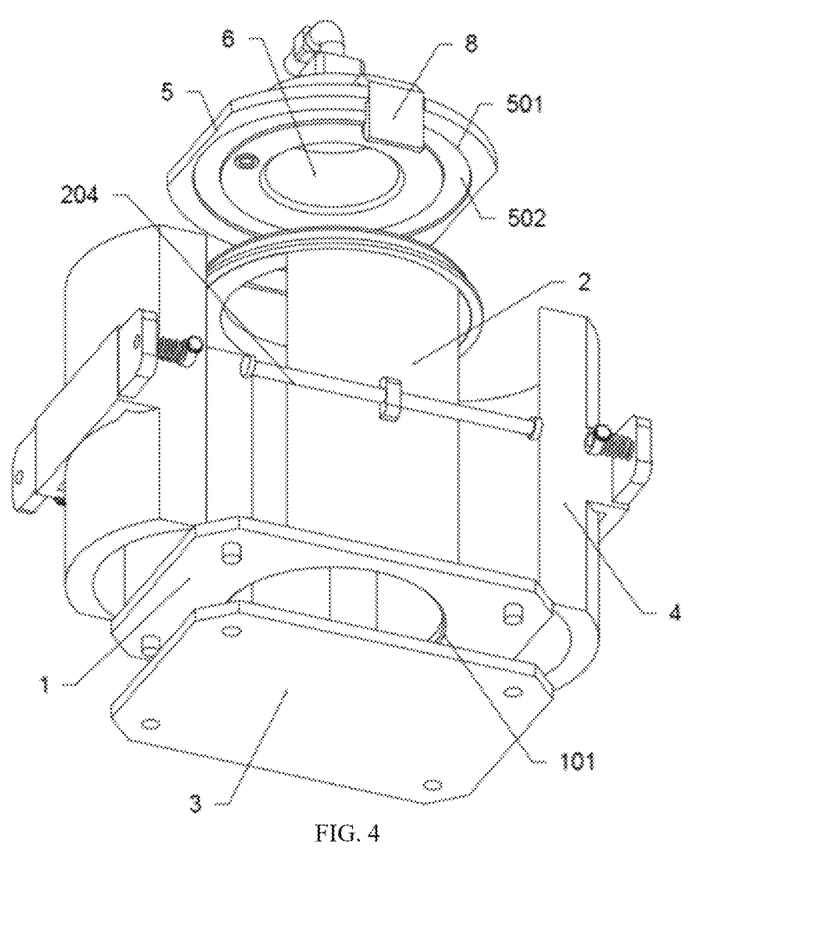
FIG. 4 shows the structure diagram at the bottom of FIG. 3 of this application.

Example I: Please refer to the FIG. 1 to the FIG. 9

Figure 7:
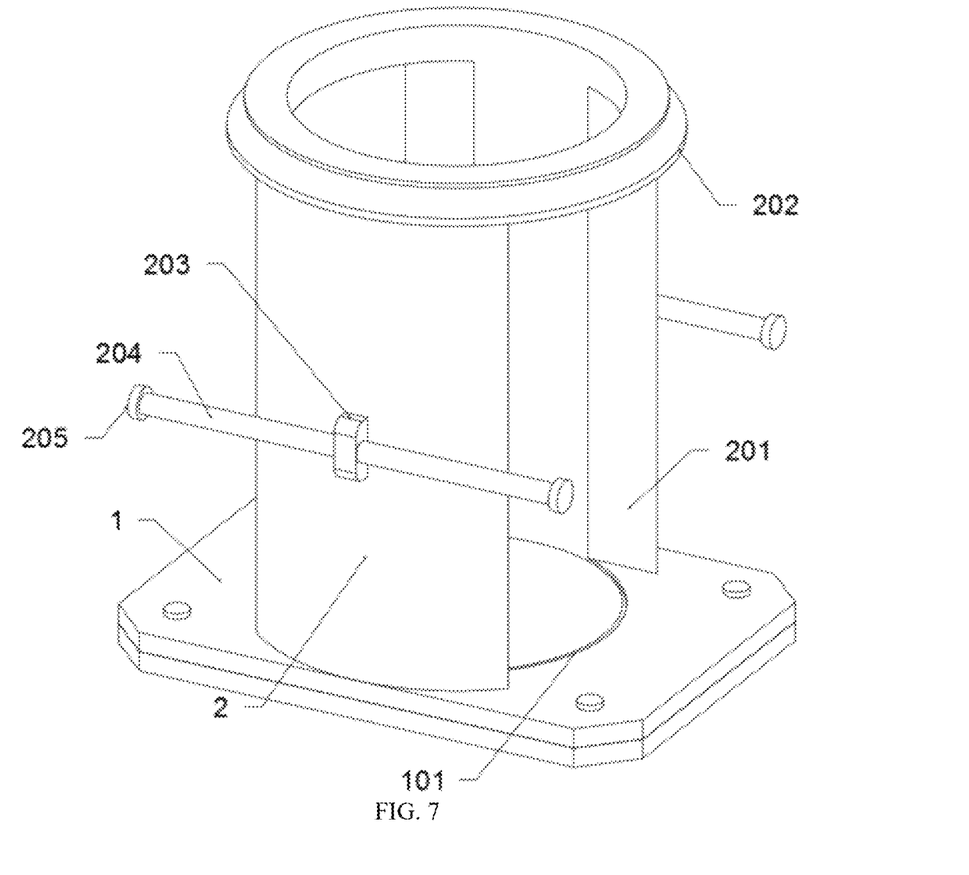
FIG. 7 shows the structure diagram of the core column storage barrel.
Figure 8:
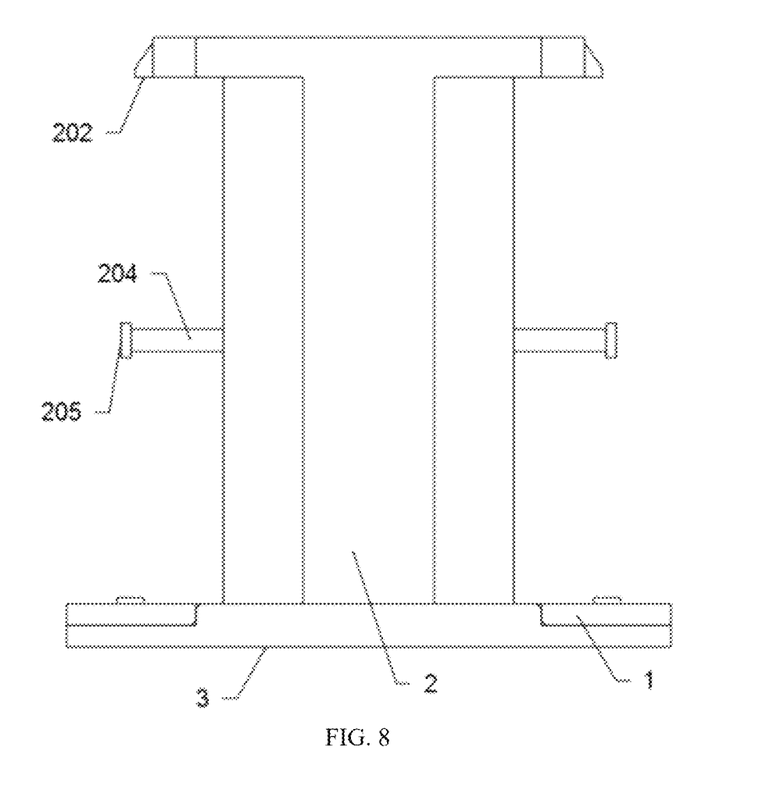
FIG. 8 shows the structure diagram of the core column storage barrel under full section condition.
Figure 9:
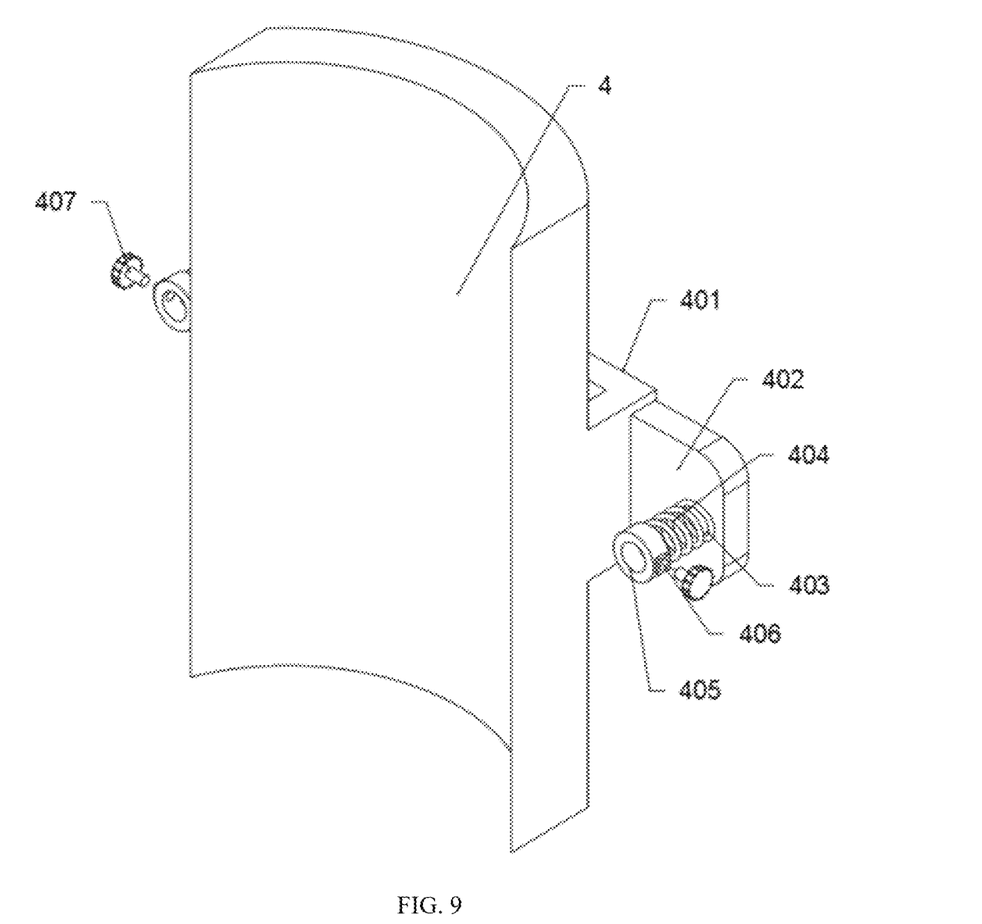
FIG. 9 shows the structure diagram of the pressure simulation push block.

The invention provides a fracture opening simulation device for hard brittle mudstone and shale with organic matter, including a simulated support 1, the lower part of the simulated support 1 is connected with a storage bucket bottom block plate 3 through a screw, the middle of the simulated support 1 is provided with a support socket 101 with a circular structure, The upper surface of the storage bucket bottom block plate 3 is provided with a circular convex structure of the block plate boss 301, the block plate boss 301 is closely inserted in the support socket 101, the upper surface of the simulated support 1 is fixed connected with a core column storage barrel 2, the axis of the core column storage barrel 2 is perpendicular to the upper surface of the simulated support 1, wherein, The core column storage barrel 2 is connected with two pressure simulation push blocks 4. The upper end of the core column storage barrel 2 is provided with a storage tube cover plate 5. The middle of the storage tube cover plate 5 is provided with a drilling fluid pressure chamber 6, and the axis of the drilling fluid pressure chamber 6 is perpendicular to the upper surface of the storage tube cover plate 5. A pressure gauge 7 is installed on the upper surface of the storage tube cover plate 5 through screws. The detection end of the pressure gauge 7 is located below the storage tube cover plate 5. The edge of the storage tube cover plate 5 is connected with two positioning lock plates 8, and the lower end of the positioning lock plate 8 is connected with the upper edge of the core column storage barrel 2.

a) In the present example, the core column storage barrel 2 is a cylindrical structure, the side wall of the core column storage barrel 2 is provided with two guide ports on a side of storage barrel 201, the side wall of the guide port on the side of storage barrel 201 is parallel to each other, the edge of the outer surface of the core column storage barrel 2 is fixed connected with the upper wedge ring 202, the cross section of the upper wedge ring 202 is a wedge-shaped structure. The inclined plane of the upper wedge ring 202 is facing outward and above; The core column used in the test is stored through the core column storage barrel 2, the lower end of the core column storage barrel 2 is fixed connected with the simulated support 1, and the support socket 101 is sealed through the block plate boss 301, thus the lower end of the core column storage barrel 2 is blocked. The outer cylinder of the core column storage barrel 2 is fixably connected with a limit connecting plate 203 in front and behind, The limit connecting plate 203 is fixed on both sides of a limit guide rod 204, the limit guide rod 204 is perpendicular to the limit connecting plate 203, the limit guide rod 204 is connected with the outer end of the guide rod limit end 205 by welding.

b) In the embodiment of the present invention, the pressure simulation push block 4 is surrounded by rubber outer layer, The pressure simulation push block 4 is sliding connected in the guide port on the side of storage barrel 201, pressure simulation push block 4 external surface is provided with a simulated push frame 401; The simulated push frame 401 front and rear respectively is fixed connected with a simulated drawing plate 402; A drawplate guide hole 403 with a circular hole structure is simulated through the simulated drawing plate 402; The simulated drawing plate 402 close to the core column storage barrel 2 center side is fixed connected with a push plate tension spring 404, the push plate tension spring 404 sockets on the limit guide rod 204, the push plate tension spring 404 is fixed connected with the outer end of a positioning lock barrel 405; The positioning lock barrel 405 is actively connected with the limit guide rod 204, the positioning lock barrel 405 is provided with a locking screw hole 406, the axis of the locking screw hole 406 is perpendicular to the limit guide rod 204, and the locking screw hole 406 is spirally connected with a locking screw column 407.

The guide port on the side of storage barrel 201 is connected with the pressure simulation push block 4, and the side wall of the core column storage barrel 2 is blocked through the pressure simulation push block 4. Under normal conditions, the simulated drawing plate 402 is pulled to the direction of the positioning lock barrel 405 through the push plate tension spring 404, and the pressure simulation push block 4 is exerted to the center of the core column storage barrel 2. When the pressure is applied to the core column inside the core column storage barrel 2, and the tension of the pressure simulation push block 4 is adjusted, the locking screw column 407 is rotated, so that the locking screw column 407 moves outward and is separated from the limit guide rod 204, the positioning lock barrel 405 slides on the limit guide rod 204, and the expansion range of the push plate tension spring 404 is adjusted. Then, the tension of the pressure simulation push block 4 was adjusted, the extrusion pressure of the core column in the core column storage barrel 2 was adjusted, and the pressure in the environment of the mudstone and shale under different depths and environmental states was simulated to change the simulation test environment.

Figure 5:
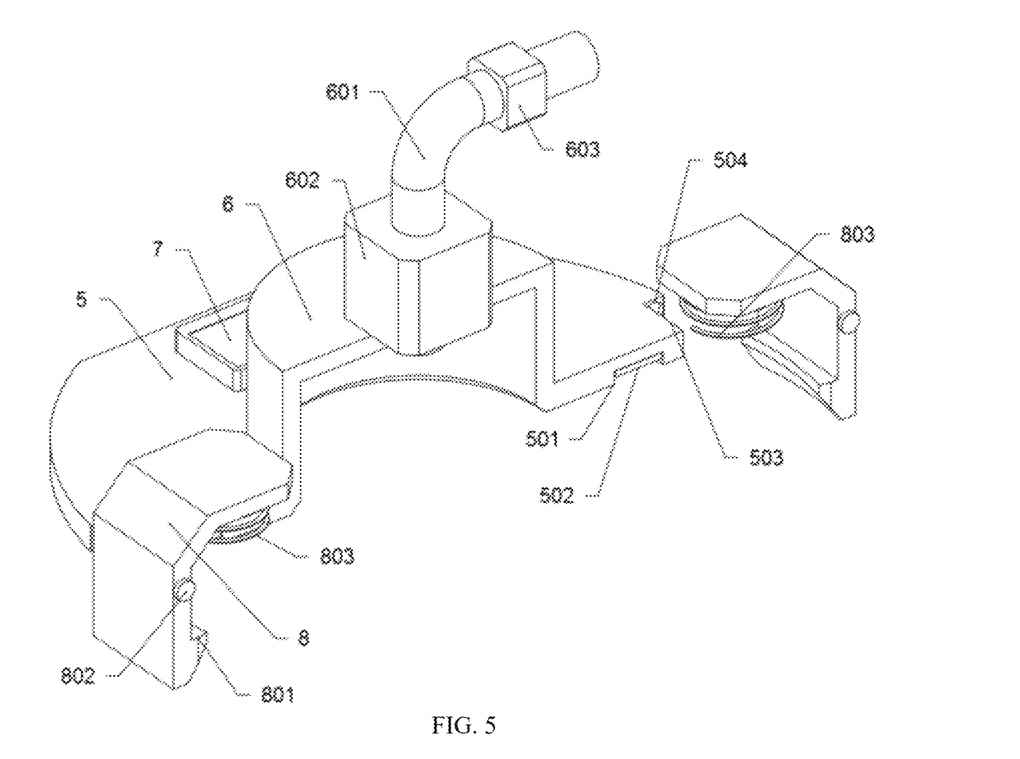
FIG. 5 shows the structure diagram of the storage tube cover plate of the application.
Figure 6:
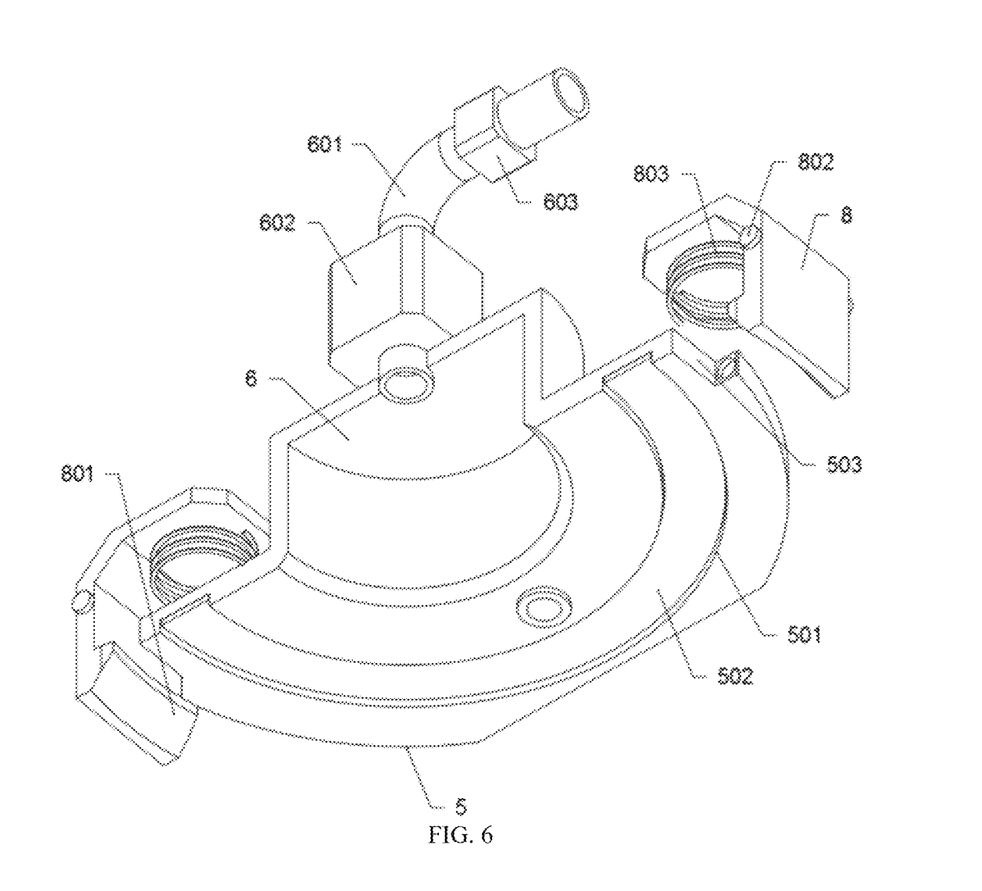
FIG. 6 shows the structure diagram of the positioning lock plate of the application.

In example 2, on the basis of Example 1, a docking ring groove 501 is arranged on the lower surface of the storage tube cover plate 5, and the inner part of the docking ring groove 501 is fixed connected with a sealing ring 502 by gluing. The edge of the storage tube cover plate 5 is arranged with two rectangular structure side mouths of the cover plate 503, and each of the side mouths of the cover plate 503 is arranged with an articulated socket 504 with a circular hole structure. The drilling fluid pressure chamber 6 is connected with a pressure input tube 601, the pressure input tube 601 is installed with a pressure pump 602, the pressure pump 602 is located above the drilling fluid pressure chamber 6, the pressure input tube 601 is installed with a flow meter 603. the positioning lock plate 8 is L-shaped structure, the positioning lock plate 8 inside the lower edge of the surface processing a locking wedge edge 801, the locking wedge edge 801 of the wedge faces toward the inner and lower side of the positioning lock plate 8, the positioning lock plate 8 is provided with two articulated end blocks 802, the articulated end block 802 rotation connected in the articulated socket 504, The positioning lock plate 8 is fixed on a lock plate spring 803, and the lower end of the lock plate spring 803 is fixed on the upper surface of the storage tube cover plate 5.

Under normal conditions, under the action of the lock plate spring 803, the lower end of the positioning lock plate 8 is attached to the core column storage barrel 2, so that the locking wedge edge 801 is attached to the outer surface of the core column storage barrel 2, and the upper wedge ring 202 is located at the lower end of the locking wedge edge 801, and the storage tube cover plate 5 is tightly covered on the top of the core column storage barrel 2 by the locking wedge edge 801. The sealing ring 502 plays a sealing role to improve the sealing of the connection area between the top edge of the core column storage barrel 2 and the storage tube cover plate 5. When the storage tube cover plate 5 is removed, the plate body of the positioning lock plate 8 is located above the storage tube cover plate 5, so that the lower end of the positioning lock plate 8 is turned outward, and the key structure between the storage tube cover plate 5 and the core column storage barrel 2 is loose. Remove the storage tube cover plate 5 from the upper end of the core column storage barrel 2.

The working principle of this embodiment is: Firstly, when the core column sample is placed inside the experimental container, when the storage tube cover plate 5 is removed, press the plate body of the positioning lock plate 8 located above the storage tube cover plate 5, so that the lower end of the positioning lock plate 8 is turned outward, so that the key structure between the storage tube cover plate 5 and the core column storage barrel 2 is loose, and the storage tube cover plate 5 is detached from the upper end of the core column storage barrel 2. Then, the core column is placed inside the core column storage barrel 2, and the storage barrel cover plate 5 is again covered over the core column storage barrel 2, so that the top edge of the core column storage barrel 2 is inserted into the docking ring groove 501, and the sealing ring 502 is attached to the top edge of the core column storage barrel 2, and the locking screw column 407 is rotated outward. Adjust the position of the positioning lock barrel 405 on the limit guide rod 204, adjust the spacing between the positioning lock barrel 405 and the simulation pull plate 402, tighten the tension spring 404 of the push plate, apply the appropriate tension to the pressure simulation push block 4, and then rotate the locking screw column 407 inward to make the locking screw column 407 and the limit guide rod 204 top tight. The positioning lock barrel 405 is fixed on the limit guide rod 204, and the tension force is continuously applied to the simulated drawing plate 402 through the push plate tension spring 404, so as to simulate the pressure under different depths and environmental conditions of the mudstone and shale in the environment. The simulated test environment is changed accordingly, and the pressure input tube 601 is connected with the drilling fluid. The drilling fluid is input into the container through the pressure pump 602, and the changes of the pressure and capacity of the drilling fluid in the container and the internal test samples are recorded. The law and influencing factors of the crack opening of hard and brittle shale can be obtained, which provides reference for practical engineering application.

In the present invention, the following points should be noted:

1. The drawings attached to the disclosed embodiment of the invention only relate to the structure related to the disclosed embodiment of the invention, and other structures can refer to the general design.

2. Without conflict, the embodiments disclosed in the invention and the features in the embodiments may be combined with each other to obtain new embodiments.

The above is only the specific implementation method disclosed by the invention, but the protection scope of the disclosure is not limited to this. Any technical personnel familiar with the technical field can easily think of changes or substitutions within the technical scope disclosed by the disclosure, which should be covered within the protection scope of the disclosure. Therefore, the scope of protection of the disclosure shall be subject to the scope of protection of the claims.

What is claimed is:

1. A fracture opening simulation device for hard brittle mudstone and shale with organic matter, it includes a simulated support, the lower part of the simulated support is connected with a storage bucket bottom block plate through a screw, the middle of the simulated support is provided with a support socket with a circular structure, the upper surface of the storage bucket bottom block plate is provided with a circular convex structure of the block plate boss, the block plate boss is inserted in the support socket, the upper surface of the simulated support is fixed connected with a core column storage barrel, the axis of the core column storage barrel is perpendicular to the upper surface of the simulated support, wherein, The core column storage barrel is connected with two pressure simulation push blocks; The upper end of the core column storage barrel is provided with a storage tube cover plate; The middle of the storage tube cover plate is provided with a drilling fluid pressure chamber, and the axis of the drilling fluid pressure chamber is perpendicular to the upper surface of the storage tube cover plate;

A pressure gauge is installed on the upper surface of the storage tube cover plate through screws; The detection end of the pressure gauge is located below the storage tube cover plate; The edge of the storage tube cover plate is connected with two positioning lock plates, and the lower end of the positioning lock plate is connected with the upper edge of the core column storage barrel;

The core column storage barrel is a cylindrical structure, the side wall of the core column storage barrel is provided with two guide ports on a side of storage barrel; The side wall of the guide port on the side of storage barrel is parallel to each other, the edge of the outer surface of the core column storage barrel is fixed connected with the upper wedge ring, the cross section of the upper wedge ring is a wedge-shaped structure; The inclined plane of the upper dswedge ring is facing outward and upward; The outer cylinder of the core column storage barrel is fixably connected with a limit connecting plate in front and behind; The limit connecting plate is fixed on both sides of a limit guide rod, the limit guide rod is perpendicular to the limit connecting plate, the limit guide rod is connected with the outer end of the guide rod limit end by welding;

The pressure simulation push block is surrounded by a rubber outer layer, the pressure simulation push block is sliding connected in the guide port on the side of storage barrel; The pressure simulation push block external surface is provided with a simulated push frame; The simulated push frame front and rear respectively is fixed connected with a simulated drawing plate; A drawplate guide hole with a circular hole structure is simulated through the simulated drawing plate; The simulated drawing plate close to the core column storage barrel center side is fixed connected with a push plate tension spring, the push plate tension spring sockets on the limit guide rod, the push plate tension spring is fixed connected with the outer end of a positioning lock barrel; The positioning lock barrel is actively connected with the limit guide rod, the positioning lock barrel is provided with a locking screw hole, the axis of the locking screw hole is perpendicular to the limit guide rod, and the locking screw hole is spirally connected with a locking screw column.

2. The fracture opening simulation device for hard brittle mudstone and shale with organic matter described in claim 1, wherein, a docking ring groove is arranged on the lower surface of the storage tube cover plate, and the inner part of the docking ring groove is fixed connected with a sealing ring by gluing; The edge of the storage tube cover plate is arranged with two rectangular structure side mouths of the cover plate, and each of the side mouth mouths of the cover plate is arranged with an articulated socket with a circular hole structure.

3. The fracture opening simulation device for hard brittle mudstone and shale with organic matter described in claim 1, wherein, The drilling fluid pressure chamber is connected with a pressure input tube, the pressure input tube is installed with a pressure pump, the pressure pump is located above the drilling fluid pressure chamber, the pressure input tube is installed with a flow meter.

4. The fracture opening simulation device for hard brittle mudstone and shale with organic matter described in claim 2, wherein, the positioning lock plate is L-shaped structure, the positioning lock plate inside the lower edge of the surface processing a locking wedge edge, the locking wedge edge of the wedge faces toward the inner and lower side of the positioning block plate, the positioning lock plate is provided with two articulated end blocks, the articulated end block rotation connected in the articulated socket, The positioning lock plate is fixed on the lock plate spring, and the lower end of the lock plate spring is fixed on the upper surface of the storage tube cover plate.

* * * * *